United States Patent [19]
Bimbo et al.

[11] Patent Number: 5,728,121
[45] Date of Patent: Mar. 17, 1998

[54] SURGICAL GRASPER DEVICES

[75] Inventors: Frank A. Bimbo, Peterborough, N.H.; Constantine Frantzides, Brookfield, Wis.; Theresa Richards, Fitchburg; Paul D. O'Connor, East Bridgewater, both of Mass.

[73] Assignee: Teleflex Medical, Inc., Plymouth Meeting, Pa.

[21] Appl. No.: 633,886

[22] Filed: Apr. 17, 1996

[51] Int. Cl.$^6$ .................................................. A61B 17/00
[52] U.S. Cl. ............................................................ 606/207
[58] Field of Search .................................. 606/51, 52, 83, 606/119, 120, 174, 205–211; 128/750–755; 294/99.2

[56] References Cited

U.S. PATENT DOCUMENTS

| | | |
|---|---|---|
| 273,382 | 3/1883 | Packham . |
| 427,555 | 5/1890 | Connor . |
| 1,422,538 | 7/1922 | Cameron . |
| 2,015,617 | 9/1935 | Claudius . |
| 2,121,989 | 6/1938 | Schnase et al. . |
| 2,631,585 | 3/1953 | Siebrandt . |
| 2,698,483 | 1/1955 | Berkowitz . |
| 2,704,668 | 3/1955 | Park, Sr. . |
| 2,757,665 | 8/1956 | Tanikawa . |
| 3,503,396 | 3/1970 | Pierie et al. ................ 606/207 |
| 3,746,002 | 7/1973 | Haller . |
| 3,868,957 | 3/1975 | Doddington . |
| 3,892,241 | 7/1975 | Laveen . |
| 3,916,908 | 11/1975 | Leveen . |
| 3,921,640 | 11/1975 | Freeborn . |
| 3,977,410 | 8/1976 | Huston et al. . |
| 4,016,883 | 4/1977 | Wright, Jr. . |
| 4,106,508 | 8/1978 | Berlin . |
| 4,122,856 | 10/1978 | Mosior et al. . |
| 4,165,747 | 8/1979 | Bermant . |
| 4,204,532 | 5/1980 | Lind et al. . |
| 4,274,415 | 6/1981 | Kanamoto et al. . |
| 4,324,248 | 4/1982 | Perlin . |
| 4,326,006 | 4/1982 | Kaminstein . |
| 4,337,774 | 7/1982 | Perlin . |
| 4,390,019 | 6/1983 | LaVeen et al. . |
| 4,478,219 | 10/1984 | Rozario et al. . |
| 4,531,519 | 7/1985 | Dunn et al. . |
| 4,571,390 | 2/1986 | Sakagami et al. . |
| 4,586,501 | 5/1986 | Claracq . |
| 4,708,140 | 11/1987 | Baron . |
| 4,735,843 | 4/1988 | Noda . |
| 4,777,950 | 10/1988 | Kees, Jr. . |
| 4,816,328 | 3/1989 | Saville et al. . |
| 4,836,205 | 6/1989 | Barrett . |
| 4,882,113 | 11/1989 | Tu et al. . |
| 4,917,960 | 4/1990 | Hornberger et al. . |
| 4,955,896 | 9/1990 | Freeman . |
| 4,973,609 | 11/1990 | Browne . |
| 4,976,721 | 12/1990 | Blasnik et al. . |

(List continued on next page.)

FOREIGN PATENT DOCUMENTS

| | | | |
|---|---|---|---|
| 0 297 771 | 1/1989 | European Pat. Off. . | |
| 0490301 | 6/1992 | European Pat. Off. ............ | 606/207 |

OTHER PUBLICATIONS

H. Lipshitz et al., *Tappi Journal*, pp. 237–245 (1990).

*Primary Examiner*—Michael Buiz
*Assistant Examiner*—William W. Lewis
*Attorney, Agent, or Firm*—David G. Conlin; Peter F. Corless

[57] ABSTRACT

The present invention provides a surgical grasper device that comprises a generally elongate housing member having a handle member at a proximal end and first and second grasping arms at a distal end. First and second grasping elements are preferably releasably attached to the first and second grasping arms respectively. The grasping elements are positioned on the arms in an opposed facing relationship to enable grasping a targeted surface such as living tissue between the elements. A gripping material at least partially covers or is otherwise incorporated into the surface of one or both of the grasping elements. The gripping material provides enhanced holding power to the targeted surface relative to the holding power provided by the grasping elements in the absence of the gripping material.

32 Claims, 5 Drawing Sheets

U.S. PATENT DOCUMENTS

| | | |
|---|---|---|
| 5,022,990 | 6/1991 | Doi et al. . |
| 5,026,382 | 6/1991 | Peiffer . |
| 5,028,332 | 7/1991 | Ohnishi . |
| 5,030,224 | 7/1991 | Wright et al. . |
| 5,037,457 | 8/1991 | Goldsmith et al. . |
| 5,079,272 | 1/1992 | Allegrezza, Jr. et al. . |
| 5,103,839 | 4/1992 | Shichman . |
| 5,133,724 | 7/1992 | Wilson, Jr. et al. . |
| 5,176,700 | 1/1993 | Brown et al. . |
| 5,217,802 | 6/1993 | Scarmoutzos . |
| 5,238,471 | 8/1993 | Blanchet-Fincher . |
| 5,238,547 | 8/1993 | Tsubouchi et al. . |
| 5,242,968 | 9/1993 | Minghetti et al. . |
| 5,254,131 | 10/1993 | Razi . |
| 5,258,005 | 11/1993 | Christian .................... 606/210 |
| 5,286,382 | 2/1994 | Scarmoutzos et al. . |
| 5,308,271 | 5/1994 | Foulke . |
| 5,340,842 | 8/1994 | Adamski et al. . |
| 5,342,393 | 8/1994 | Stack . |
| 5,352,235 | 10/1994 | Koros et al. . |
| 5,356,466 | 10/1994 | Lawson . |
| 5,383,895 | 1/1995 | Holmes et al. . |
| 5,403,483 | 4/1995 | Hayashida et al. . |
| 5,405,618 | 4/1995 | Buttery et al. . |
| 5,439,476 | 8/1995 | Frantzides . |
| 5,536,251 | 7/1996 | Evard et al. ................... 606/211 |

SURGICAL GRASPER DEVICES

BACKGROUND OF THE INVENTION

1. Field of the Invention

The present invention relates to surgical grasper devices, particularly grasper devices suited for laparoscopic and other endoscopic procedures.

2. Background

Endoscopic surgeries such as laparoscopic and thoracoscopic procedures have been developed relatively recently as a less invasive alternative to traditional open surgeries. For example, laparoscopic procedures typically involve one or more relatively small (e.g. about 5 to 12 mm) incisions in a patient's abdominal area to provide entry for various surgical instruments including cutting, grasping and positioning instruments as well as viewing devices to enable the physician to perform the surgery. Numerous surgical procedures are currently performed by laparoscopic or other endoscopic techniques including e.g. intestinal and stomach operations such as removal of colon cancer or relief of chronic heartburn, hernia repairs, removal of gall bladder or other gall bladder operations, Ob/Gyn related surgeries and other procedures such as involving manipulations of a patient's spleen, liver, lung, heart, etc. See generally U.S. Pat. Nos. 5,439,476; 5,383,895; 5,352,235; and 5,258,005.

Traditionally, in open surgeries the surgeon's hands are used to manipulate and retract tissue. In contrast, in the minimally invasive approach grasping forceps are more often used. A number of grasping devices have been employed for performing such surgical procedures, e.g., to hold and move one or more of a patient's organs or other tissue so the physician can carry out the desired surgery. However, prior endoscopic grasping devices often may puncture, bruise or otherwise may cause long-term trauma to the manipulated tissue. Such injury complicates and prolongs a patient's recovery and can impair the function of the damaged tissue. In some cases, the trauma can also substantially complicate the surgery in which it occurs. Indeed, if the trauma is severe, an additional endoscopic procedure or even an open surgery may be required to repair the damaged tissue. For example, a stomach wall tear may cause bleeding and/or perforation and require one or more stitches. In the case of removal of the gall bladder, if this organ is perforated, infected bile can leak into the abdominal cavity and cause an infection or other problems.

Moreover, irrespective of the trauma involved with use of prior devices, many devices have not provided satisfactory holding power to some types of tissue, thereby limiting their utility in various procedures or at a minimum complicating the surgeon's work. Tissue that must be manipulated during a surgical procedure can have relatively widely varying surface characteristics and can be highly slippery and difficult to grasp or move.

Additionally, such prior devices that provide limited holding power may force a physician to use significant grasping pressure in order to manipulate tissue as required to perform the surgical procedure. Use of such high grasping pressures can result in increased long-term trauma to the tissue.

Still further, many prior endoscopic grasping devices have sharp or hard surfaces that contact the manipulated tissue. Those surfaces often will puncture or otherwise injure the manipulated tissue.

It thus would be desirable to have a new atraumatic surgical grasper device, i.e. a device that does not generally cause significant (long-term) trauma to manipulated tissue of a patient during use. It would be further desirable to have such a grasper device where the device is suitable for laparoscopic and other endoscopic procedures and provides good gripping action to a variety of tissue types with only minimal grasping pressure.

SUMMARY OF THE INVENTION

The present invention comprises an improved surgical grasping device that exhibits enhanced gripping of a variety of types of tissue at minimal grasping pressures. The device is suitable for use in laparoscopic and other endoscopic procedures and preferably includes replaceable grasping elements that incorporate a surface gripping material that holds well in a wet environment to a target surface such as, but not limited to living tissue. Some aspects of the present invention involve the discovery and use of gripping materials having the unexpected enhanced capability to grip and manipulate living tissue having a wide variety of surface characteristics. For example, preferred gripping materials provide good holding power and the ability to manipulate as desired stomach, intestinal, gall bladder, ovarian, vascular and lung tissue. Those types of tissue in many cases have been difficult to manipulate atraumatically with prior grasper devices without damaging tissue.

A device of the invention comprises a generally elongate housing member having a handle member at a proximal end and first and second grasping arms at a distal end. A pair of grasping elements are preferably releasably attached to the grasping arms. The grasping elements are positioned on the arms in an opposed facing relationship to enable grasping a targeted surface such as living tissue between the elements. A gripping material that is preferably substantially smooth and at least partially covers or is otherwise incorporated into the exposed surface of one or both of the grasping elements. The gripping material provides enhanced holding power or gripping ability to the targeted surface relative to the holding power provided by the grasping elements in the absence of the gripping material. For example, such enhanced holding power can be verified by testing the ability of a grasping device of the invention (that includes the gripping material) to grip tissue such as stomach at a particular grasping pressure, relative to the ability of the same grasping device but without the gripping material to grip to the same tissue at the same grasping pressure. Enhanced holding power would e.g. enable grasping the tissue without slippage whereas slippage of the tissue would be seen with the device without the gripping material.

Devices of the invention are preferably reusable, i.e. the device can be used in multiple surgical procedures with replacement of grasping elements that are removably attached to the device's grasping arms. In one preferred embodiment, the grasping elements will be supplied separately from the device, with the elements preferably packaged in sterile condition. The device itself (without pad elements) can be cleaned and a new, sterile set of pads applied prior to each use of the device. Such a reusable system provides substantial cost and waste savings relative to a grasper devices that is entirely disposed of after a single use.

In other aspects, the invention provides surgical grasping devices of the type described herein wherein the grasping elements are not readily removable or are "permanently affixed" and would not be removed before or after typical use of the device. These devices may be disposable, i.e. the entire device is discarded after a single use, or the devices may be reusable wherein the entire device is cleaned and sterilized after use in a surgical procedure. By stating that the elements are "permanently affixed" it is intended that the elements are not readily removable during normal use of the device.

It has been found that grasping devices of the invention are atraumatic, i.e. the devices generally do not cause substantial trauma of manipulated tissue (e.g. bruising, tearing, etc.), even under stringent conditions. For example, a grasper of the invention and two different commercially available laparoscopic graspers were tightened to the same grasping pressure on stomach tissue and left in place for approximately 2.75 hours. One commercial device left severely bruised tissue without puncture, while the other commercial device actually punctured the manipulated stomach tissue. In marked contrast, the grasper device of the invention left no bruising or other lasting signs of trauma on the stomach tissue.

The invention further provides methods for carrying out various surgical procedures, including laparoscopic and other endoscopic surgeries, comprising use of a grasper device of the invention.

Other aspects of the invention are disclosed infra.

BRIEF DESCRIPTION OF DRAWINGS

FIGS. 4A, 4D and 4E are side views and FIGS. 4B and 4C are top views;

FIG. 5A is a side view with the grasping element, attachment component and grasping arm disassembled; FIG. 5B is a partially disassembled view with the attachment component nested within the grasping element; FIG. 5C is an assembled view with the nested attachment component releasably secured in the grasping arm; and FIG. 5D is a further assembled view of the distal end of a device of the invention.

DETAILED DESCRIPTION OF THE INVENTION

Figure 1:
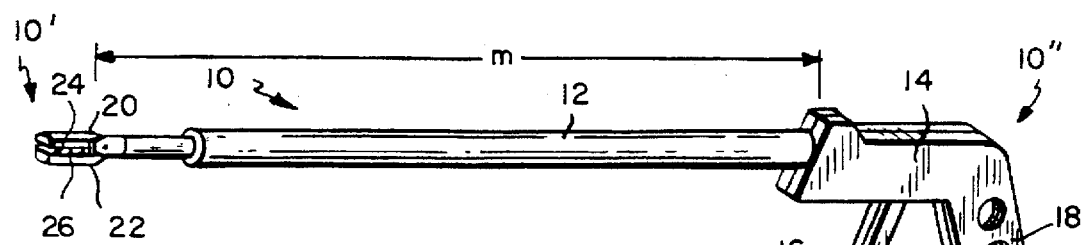
FIG. 1 shows an above view of a preferred grasper device of the invention with the grasper arms in a closed position.

Referring now to the Drawings, where particularly preferred devices of the invention are depicted, FIG. 1 shows grasper device 10 that includes an elongate body member 12, handle member 14 that includes actuating handles 16 and 18 at the device proximal end, and grasping arms 20 and 22 with replaceable pads 24 and 26 at the device distal end 10'. (In accordance with conventional practice, "proximal end" designates herein the specified end closest to the medical personnel manipulating the device, and "distal end" designates herein the opposite end placed within a patient.)

Actuating handles 16 and 18 are adapted to be held in a user's single hand and preferably include finger and thumb rings as depicted in FIG. 1. Handle member 14 also includes ratchet racks 28 for releasable securing of grasping arms 20 and 22 at a desired position. In use, grasping arms 20 and 22 are firmly held in a given position by locking of ratchets 28. Arms 20 and 22 then may be moved to different positions by alternate unlocking and locking of ratchets 28.

Body member 12 is suitably a hollow tube that contains along its length a push/pull rod that drives a cam activated by handle arm 16 to open and close grasping arms 20 and 22 via a central pivot point as discussed below. Other mechanisms to activate the grasping arms also could be employed.

Figure 2A:
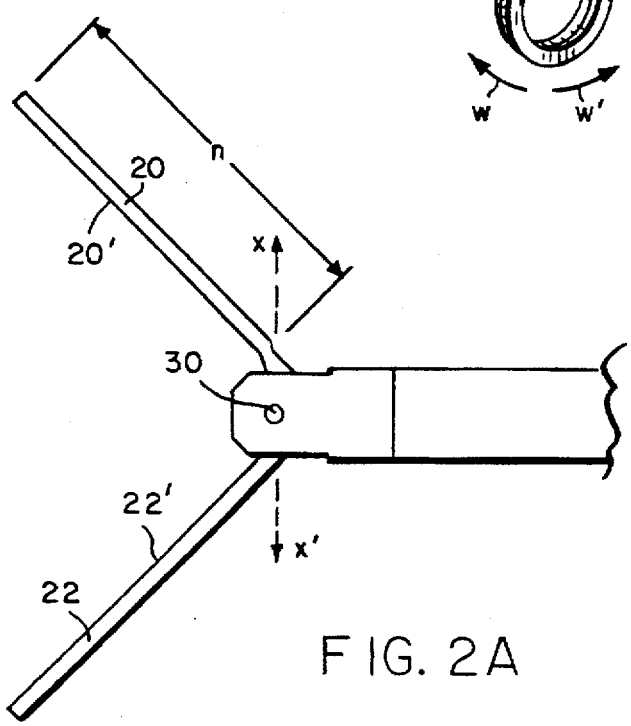
FIGS. 2A–2B show side views of the distal end of a preferred grasper device of the invention without the replaceable elements attached to the grasper arms and with the arms in an open position (FIG. 2A) and a closed position (FIG. 2B)
Figure 2B:
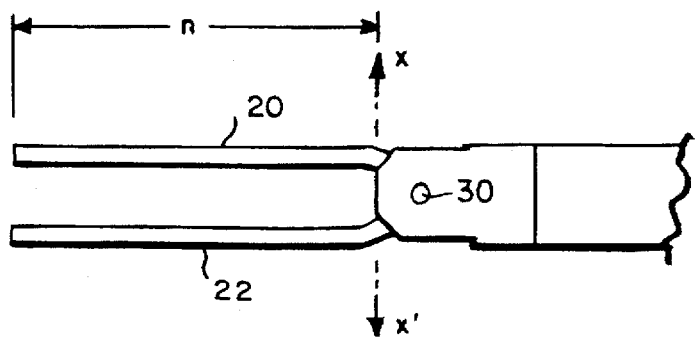

Device 10 includes the pair of grasping arms 20 and 22 and that can move, alone or in combination, with respect to each other to enable grasping of a targeted object. As depicted in FIGS. 2A and 2B, arms 20 and 22 can each move in opposed directions from a center pivot point 30 to enable grasping of a targeted object. A single action system also may be suitable, i.e. where one of arms 20 and 22 remains stationary and the other grasping arm moves toward and away from the stationary arm. Arms 20 and 22 preferably extend or open to at least a 90° angle with respect to one another as shown in FIG. 2A. Also, rather than dual or single action movement from a pivot point, other configurations of arms 20 and 22 will be suitable, e.g., the entire length of the arms could move laterally (i.e. directions x and x' in FIGS. 2A and 2B) with respect to point 30 rather than pivot around that point 30.

Grasping elements 24 and 26 are attached to inside faces 20' and 22' of respective arms 20 and 22. Preferably, elements 24 and 26 are formed of relatively soft materials to avoid bruising or other trauma to manipulated tissue during use of the device. A rubber or thermoplastic elastomeric material is particularly preferred, especially the material sold under the tradename of DYNAFLEX D-series (styrene-butadiene elastomer sold by GLS Co.). Also suitable will be material sold under the name of DYNAFLEX G-series (styrene-ethylene/butylene-styrene copolymer sold by GLS Co.). Other thermoplastic elastomers also will be suitable including C-flex, SANPREN and the like. Additional acceptable materials for forming the grasping elements will be silicones, latex and other man-made rubber materials.

Figure 3A:
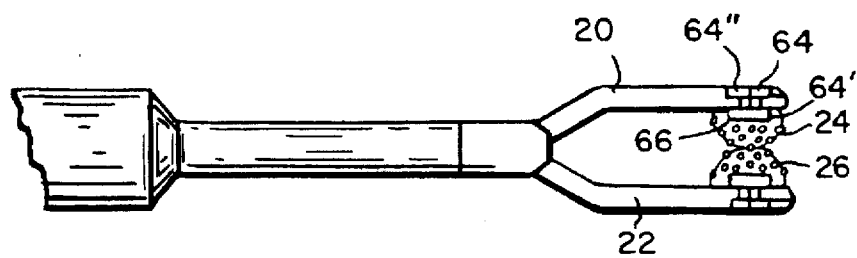
FIGS. 3A–3D show views of distal ends of additional preferred grasper devices of the invention in both the closed (FIGS, 3A and 3C) and open (FIGS. 3B and 3D) positions.
Figure 3B:
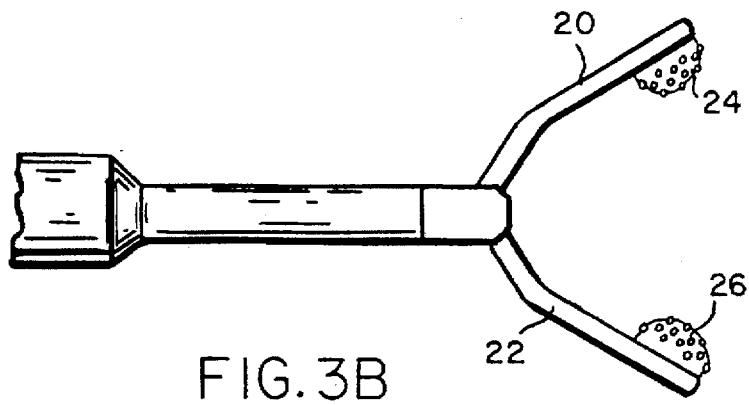
Figure 3C:
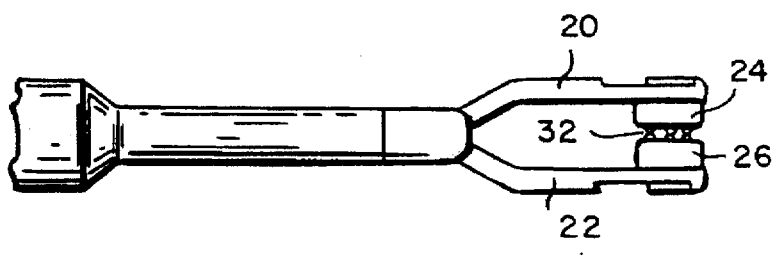
Figure 3D:
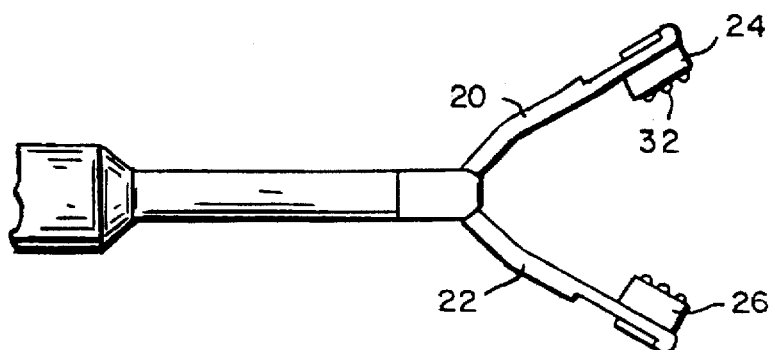
Figure 4A:
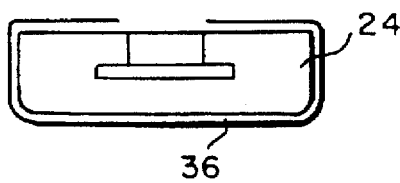
FIGS. 4A–4E show selected suitable grasping elements of devices of the invention.
Figure 4B:
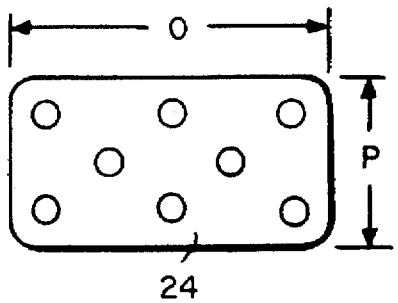
Figure 4C:
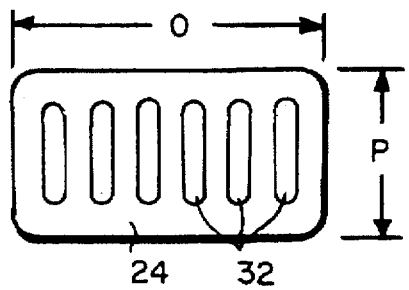
Figure 4D:
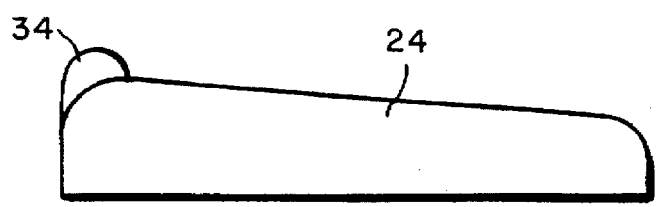
Figure 4E:
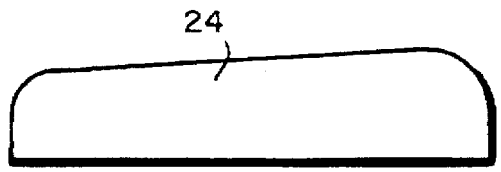

As shown in FIGS. 3A–3D and 4A–4E, the grasping elements or pads may have a variety of configurations as may be desired. Thus, for example, the elements may comprise topography to facilitate grasping such as a series of raised bumps as depicted in FIGS. 3A, 3B and 4B, multiple ribs 32 as shown in FIG. 4C, one or more raised lips 34 as shown in FIGS. 4D, or a relatively smooth surface as shown in FIG. 4E. A preferred design is shown in FIGS. 4D and 5A–5C, where a single lip is positioned on the pad distal end, The pad elements also may have a smooth surface without any such ribs, lips or other topography, e.g. as shown in FIG. 4A, or more preferably the design shown in FIG. 4E. Such non-ribbed grasping elements may be preferable for manipulations of particularly delicate organs such as liver or lung. Also, the grasping elements suitably may have slanted faces, particularly downwardly tapering toward the device proximal end as exemplified by pad 24 depicted in FIGS. 4D, 4E and 5A–5D. Preferably the elements are of a size sufficient to overlap or cover the grasper arms when attached thereto so that no metal grasping element surfaces are exposed that could potentially pinch or otherwise cause trauma to tissue.

The grasping elements preferably will be white or other bright color for easy visibility and will be radiopaque to enable ready identification and location if an element inadvertently remains in a patient's body after surgery is completed.

At least one and preferably both of elements 24 and 26 incorporates a gripping material 36 on its exposed surface. Gripping material 36 may be a separate material that at least partially covers or encases one or both of the grasping elements. Gripping material 36 also may be an integral material of construction of the grasping element, or the preformed grasping element may be subjected to a surface modification treatment to provide the desired gripping properties. Preferably material 36 covers or is incorporated into the element so that the gripping material is present on a sufficient amount of the exposed surface of a grasping element to provide the desired holding effect. For example, preferably material 36 covers or is incorporated into the element so that the gripping material is present on at least about 50 or 70 percent or more of the entire exposed surface of a grasping element, or even more preferably material 36 covers or other is incorporated into essentially or completely the entire exposed surface of an element as generally depicted in FIG. 4A. As referred to herein, the exposed surface of a grasping element is the surface not contacting or otherwise abutting grasping arm faces 20' or 22'.

Gripping material 36 may be affixed or otherwise incorporated into elements 24 and 26 by any of a number of methods. For example, material 36 may be directly thermo-bonded to the grasping elements, particularly where material 36 and elements 24 and 26 have similar melt properties. Material 36 also may be directly solvent bonded to the grasping elements. Alternatively, material 36 may be affixed to elements 24 and 26 by a suitable adhesive, although for internal surgical applications use of an adhesive may be less preferred than a thermobond attachment. Material 36 also may be mechanically attached to the grasping elements e.g. by interweaving of the material through the grasping element/arm releasable attachment mechanism as discussed below. Also, as discussed above, material 36 may be directly integrated into a grasping element, e.g. a grasping pad element 24 may be formed from a polymer mixture that includes a polymeric gripping material, such as those materials discussed below, so that the surface of the formed element exhibits enhanced holding power to living tissue relative to the element formed without the gripping material.

Gripping material 36 suitably may be a variety of materials but should provide good atraumatic holding power to a variety of tissue types in a wet environment as would be encountered during a surgical procedure. For example, and as discussed above, preferred gripping materials provide good holding power and the ability to manipulate stomach, intestinal, gall bladder and ovarian tissue (among others), but generally without causing substantial long-term trauma to the tissue such as puncturing or significant bruising. Moreover, with the preferred grasping materials, any slippage of tissue positioned between grasping elements 24 and 26 that may ever occur should not cause significant abrading or other trauma to the tissue. Also, preferably, material 36 will provide good holding power to a variety of tissue types even after prolonged exposure to the wet environment of a surgical procedure, e.g. exposure for periods of 2 to 4 hours or more.

Material 36 suitably may be a polymer, e.g. polyvinyldiene fluoride (PVDF); or a non-woven material, e.g. high-density polyethylenes such as TYVEK; or spunbonded materials such as a polyester membrane material, e.g. Ahlstorm's 3283 product or Reemay's 2040 product; and the like. Non-polymeric materials also will be suitable, e.g. a sintered metal membrane. A sintered metal gripping material also may provide some mechanical benefits as a result of the fine rough surface of such materials. Suitable sintered metal membranes are commercially available from vendors such as Union Carbide.

Material 36 suitably may be either a hydrophilic or hydrophobic material provided the material maintains its gripping properties after being wetted out during use in a surgical procedure. However, hydrophobic materials will tend to be more durable in such wet environments and therefore will be generally preferred.

Gripping material 36 preferably will be a porous polymeric material or a non-woven material having a relative area surface roughness of between about 1.03 and 10.5, more preferably a relative area surface roughness of between about 1.08 and 4.5. See H. Lipshitz et al., *Tappi Journal*, pages 237–245 (October 1990), incorporated herein by reference, for a discussion of relative area surface roughness and the determination thereof. Preferred porous materials will have a pore size of about 200 microns or less, more preferably about 40 microns or less, preferably with a minimum size of about 0.05 microns. A particularly preferred gripping material is a PVDF material having a 2 micron pore size sold under the tradename of DURAPEL by the Millipore Corporation of Bedford, Mass. The Reemay 2040 material (having about 10 micron pore size) is also a preferred gripping material.

Preferably, material 36 will exhibit a coefficient of friction of about 0.07 or greater, more preferably about 0.09 or greater, still more preferably about 0.6 or greater. Generally preferred materials will typically have a coefficient of friction of less than about 3, more typically less than about 2. The coefficient of friction of a particular material can be readily determined by standard procedures, specifically the sled test of the American Society for Testing and Materials (ASTM) Standard Test Method for Static and Kinetic Coefficients of Friction (test designation D 1894; modified to use sled on wet pig stomach tissue).

It also should be appreciated that the gripping material on the surface of a grasping element is preferably substantially smooth and provides good gripping properties without the type of visible (naked eye) protrusions reported in certain prior clamp systems. See for instance European Application 256966 (reports VELCRO surface) and U.S. Pat. No. 3,746,002 (reports surface pin members that puncture clamped tissue). Among other things, such protrusions could result in significant trauma to manipulated tissue. References herein to a substantially smooth surface of a gripping material are intended to exclude those visible protrusions.

Elements 24 and 26, covered with material 36, may be releasably attached to arms 20 and 22 by a variety of mechanisms. The mechanism preferably should permit snap-in attachment of a grasping pad element that can be readily performed by a medical personnel and enable pad removal at the end of a medical procedure with minimal or no use of tools.

Figure 5A:
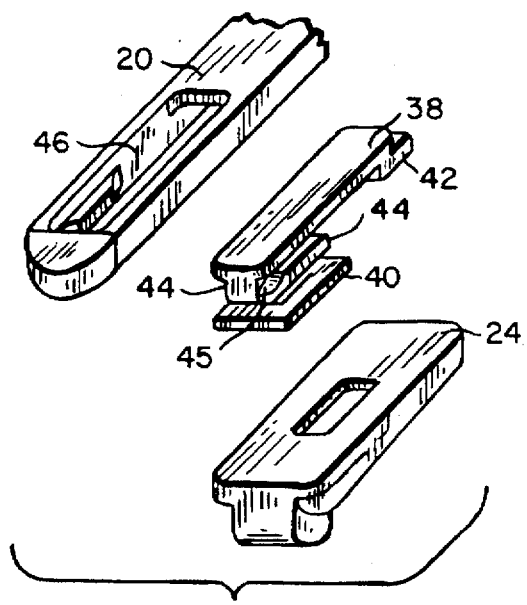
FIGS. 5A–5D show preferred grasping element attachments for devices of the invention.
Figure 5B:
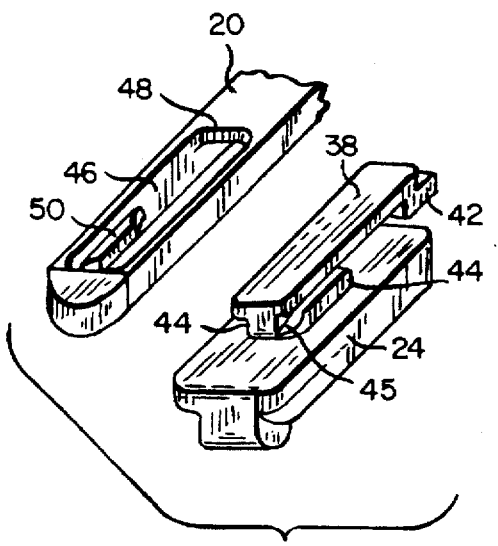
Figure 5C:
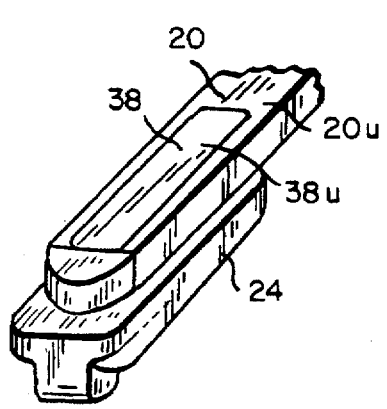
Figure 5D:
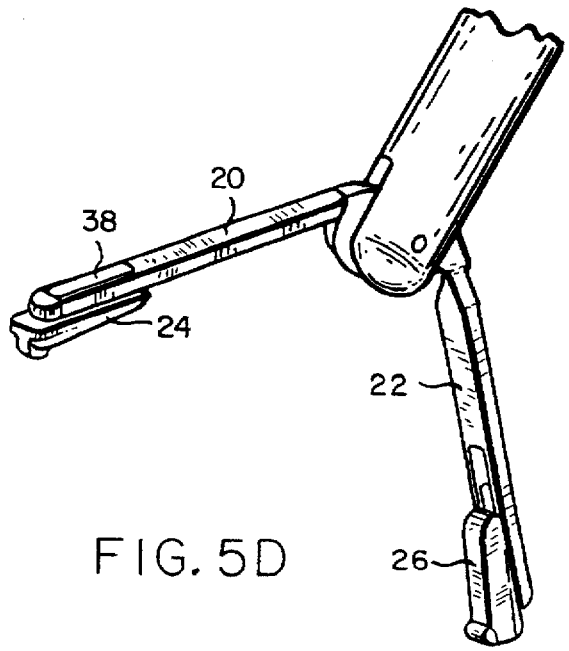

A particularly preferred attachment assembly is shown in FIGS. 5A–5D. As shown in FIG. 5A, a separate releasable lock component 38 is employed that includes a grasping element attachment portion 40 adapted to nest securely within a nesting opening 46 of element 24 or 26. Component 38 further includes a rear latch or flange 42 and side latches or flanges 44 on each side of the component 38, which are all adapted to releasably engage a grasping arm 20 or 22. Specifically, as shown in FIGS. 5B and 5C, latch 42 suitably extends through slot or opening 46 of grasping arm 20 and slides toward grasping arm proximal end to releasably lock under arm front flange 48. Side latches 44 form grooves 45 and each slide and releasably engage or lock under opposed grasping arm flanges or rail 50 of arm 20 or 22. The assembled snap-fit attachment provides a flush outer or top surface (opposite the exposed grasping element surface) of arm 20 as shown in FIG. 5C. That flush outer surface also provides visual indication that the grasping element is positioned properly within the grasping arm, i.e. an irregular surface at the interface of outer surface 20u of arm 20 and outer surface 38u of element 38 would indicate that element 38 was not properly positioned within arm 20.

Figure 6A:
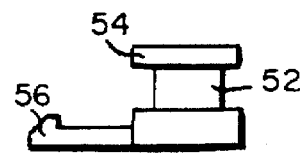
FIGS. 6A–6D show selected additional suitable grasping element attachments for devices of the invention.
Figure 6B:
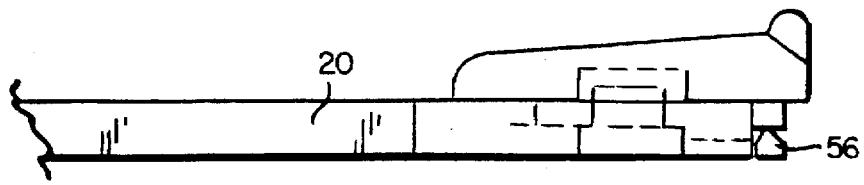
Figure 6C:
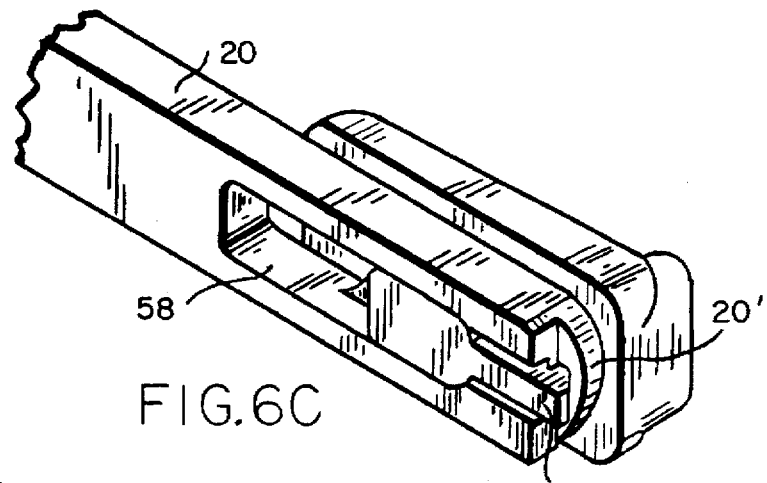
Figure 6D:
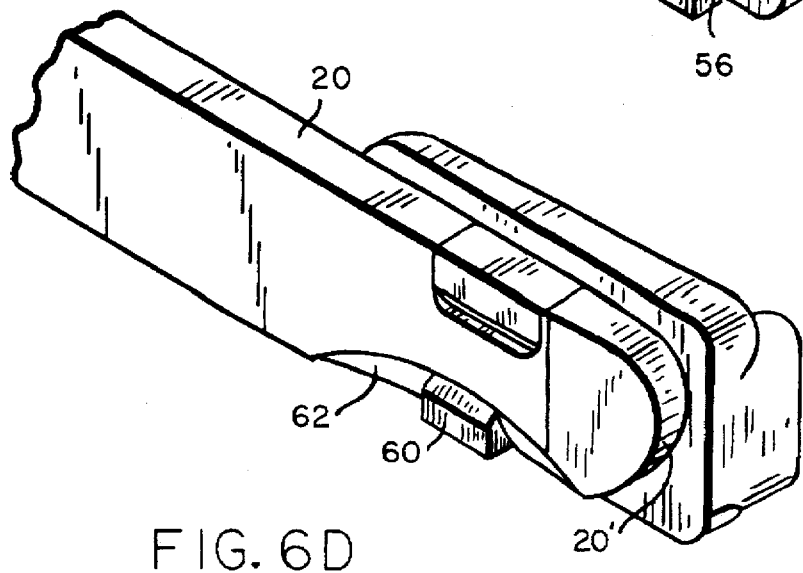

Other suitable assemblies which include a releasable latch system are shown in FIGS. 6A-6D. Specifically, as shown in FIGS. 6A-6C, a separate releasable lock component 52 can be employed that includes a grasping element attachment portion 54 adapted to nest securely within an element 24 or 26 and a protruding hitch or latch 56 adapted to releasably engage a grasping arm 20 or 22. As shown in FIGS. 6B and 6C, latch 56 suitably extends through slot 58 of arm 20 and slides toward grasping arm distal end 20' to releasably lock around that distal end. Other releasable latch or hook-type designs may be employed such as side latch 60 that extends from a side of a lock component 52 and releasably engages side 5 face 62 of an arm 20 as depicted in FIG. 6D.

Component 38 or 52, including respective portions 40 or 54 thereof, may be suitably formed of a variety of materials such as polyethylene, polypropylene or a nylon or other engineering plastics such as polycarbonate, ABS, etc. A nylon may be more preferred for its durability.

The grasping element may be affixed to the lock component by a variety of methods. For example, an insert molding process can be employed, where the grasping pad is formed around the preformed lock component. It is also preferable that attachment portion 40 or 54 be intimately thermally bonded to the grasping element in addition to the mechanical-type attachment provided by nesting the portion 40 or 54 within the element as can be seen in FIGS. 5B and 6B. For example, if elements 24 and 26 are formed from the DYNAFLEX D-series material, component 38 or 52, and particularly respective portions 40 or 54 thereof, may be suitably formed of a polyethylene or polypropylene to provide such thermal bonding of the materials.

Other suitable releasable attachment mechanisms include a tab 64 as shown in FIG. 3A that has a first end 64' with flange 66 that snap fits into a grasping element 24 or 26 and a second end 64" that slides into and engages a receiving slot in each of grasping arm top faces 20' and 22'.

Suitable dimensions of grasper devices of the invention and the components thereof can vary rather widely and can be readily determined by those skilled in the art based on the present disclosure. In general, the device should have a shape and length so that the device is capable of being inserted into a patient for use in surgical procedures, particularly endoscopic procedures. The usable length of device 10 (length m in FIG. 1) suitably may be from about 24 to about 45 cm. Suitable diameters of elongate body member 12 are 5 mm and 10 mm, particularly for laparoscopic applications, although again other diameters could be employed. For example, diameters of body member 12 within the range of 3 to 12 mm will be suitable for various applications. Grasping arms 20 and 22 preferably should be a length sufficient to accommodate releasable attachment of elements 24 and 26 as disclosed herein and suitably may be from about 6 to about 86 mm in length (length n in FIGS. 2A and 2B), more typically about 2 to about 4 cm in length. Elements 24 and 26 also preferably should be a size and width sufficient to releasably attach to arms 20 and 22 and suitably may be from about 2 to about 86 mm long (length o in FIGS. 4B and 4C) and from about 3 to about 12 mm wide (width p in FIGS. 4B and 4C).

A particularly preferred grasper device of the invention is of the configuration shown in the Drawings (particularly FIG. 1 as well as FIGS. 5A-5C with respect to releasable attachment of pad elements 24 and 26), wherein the usable length of device 10 (length m) is 32 cm; grasping arms 20 and 22 are each 1.29 inches long (length n); and elements 24 and 26 are each 0.5 inches long (length o) and 0.28 inches wide (width p).

A grasper device of the invention may be suitably used as follows in a laparoscopic, thoracoscopic or other endoscopic procedure. The grasper device can be introduced into a patient through a trocar sheath (e.g. 10 mm size). For some procedures a trocar suitably may not be employed. During insertion and positioning of device 10, arms 20 and 22 suitably will be in a closed position to provide a narrow profile with actuating handle 16 retracted toward the device proximal end 10". The distal end of the device is then maneuvered to a desired position within a patient by the surgeon grasping actuating handles 16 and 18 in a single hand and directing arms 20 and 22 to the tissue to be manipulated with aid of a laparoscopic viewing device. The physician then can open arms 20 and 22 by opening actuating handle 16 toward the distal end of the device (i.e. direction w shown in FIG. 1). The tissue to be manipulated, e.g. a stomach wall, gall bladder, intestine, etc., is positioned between arms 20 and 22 and the tissue is grasped by retracting actuating handle 16 toward the device proximal end (direction w' in FIG. 1). Grasping arms 20 and 22 may be maintained in a desired position by locking of handles 16 and 18 with ratchets 28 as discussed above.

As discussed above, it has been found that only minimal grasping pressure is required to hold and manipulate as desired a variety of tissue including e.g. gall bladder, intestines and stomach.

After completion of the desired procedure, the device can then be removed from the patient through the trocar introducer device.

Device 10 may be supplied in a variety of sizes, including different lengths as well as different diameters of the elongate body member 12 as discussed above, depending on the specific intended application.

The invention also includes device kits which comprise a grasper of the invention supplied together with or separately from grasping elements packaged in a sterile condition. Preferably, a grasper device of the invention without releasable pads is supplied separately from grasping pad elements packaged in sterile condition. Preferably two grasping elements will be supplied in a given sterile packaging.

The foregoing description of the invention is merely illustrative thereof, and it is understood that variations and modifications can be made without departing from the spirit or scope of the invention as set forth in the following claims.

What is claimed is:

1. A surgical grasper device comprising:
   an elongate housing member having a handle member at a proximal end and first and second grasping arms at a distal end;
   first and second grasping elements attached to the first and second grasping arms respectively, and positioned on the arms in an opposed facing relationship to enable grasping of a targeted surface between the elements; and
   a gripping material on one or both of the grasping elements, the material providing enhanced holding power to the targeted surface relative to the holding power provided by the elements in the absence of the gripping material.

2. The surgical grasper device of claim 1 wherein at least one of the grasping elements is releasably attached to the respective grasping arm.

3. The surgical grasper device of claim 1 wherein the grasping element is releasably attached to the arm by a flange.

4. The surgical grasper device of claim 1 wherein at least one of the grasping arms contains an internal flange to releasably engage the respective grasping element.

5. The surgical grasper device of claim 4 wherein the grasping arm comprises opposed flanges within an opening of the grasping arm to releasably engage the grasping element.

6. The surgical grasper device of claim 5 wherein the grasping element comprises opposed recessed surfaces to receive and releasably engage the opposed flanges of the grasping arm.

7. The surgical grasper device of claim 2 wherein at least one of the grasping elements is releasably attached to the grasping arm by a protrusion of the grasping element.

8. The surgical grasper device of claim 2 wherein at least one of the grasping elements is releasably secured to the grasping arm and provides visual indication that the grasping element and arm are in a desired releasably attached arrangement.

9. The surgical grasper device of claim 8 wherein the grasping element and arm are releasably secured to provide a substantially smooth top surface opposite of the exposed grasping element surface.

10. The surgical grasper device of claim 2 wherein at least one of the grasping elements is adapted to releasably attach in a single configuration to the respective grasping arm.

11. The surgical grasper device of claim 1 wherein the device is reusable for multiple surgical procedures.

12. The surgical grasper device of claim 1 wherein the device is reusable for multiple surgical procedures and the grasping elements are permanently affixed to the grasping arms.

13. The surgical grasper device of claim 1 wherein the device is disposed of after a single surgical procedure and the grasping elements are permanently affixed to the grasping arms.

14. The surgical grasper device of claim 1 wherein the gripping material is a separate material attached to the grasping element.

15. The surgical grasper device of claim 1 wherein the gripping material is an integral component of the grasping element.

16. The surgical grasper device of claim 1 wherein the gripping material is formed from one or more polymers or from a sintered metal.

17. The surgical grasper device of claim 1 wherein the gripping material is hydrophobic and porous.

18. The surgical grasper device of claim 1 wherein the gripping material has a coefficient of friction of about 0.6 or greater.

19. The surgical grasper device of claim 1 wherein the gripping material is a porous polyvinyldiene fluoride.

20. The surgical grasper device of claim 1 wherein the gripping material is substantially smooth.

21. The surgical grasper device of claim 1 wherein the grasping elements are each formed from an elastomeric material.

22. The surgical grasper device of claim 1 wherein the grasping elements comprise radiopaque material.

23. A endoscopic surgical grasper device comprising:
   an elongate housing member having a handle member at a proximal end and first and second grasping arms at a distal end;
   first and second grasping elements releasably attached to the first and second grasping arms respectively, and positioned on the arms in an opposed facing relationship to enable grasping a targeted surface between the elements.

24. The surgical grasper device of claim 23 wherein the grasping elements are releasably attached to the arms by a latch.

25. The surgical grasper device of claim 23 wherein the gripping material is substantially smooth.

26. The surgical grasper device of claim 25 wherein the gripping material has a coefficient of friction of about 0.6 or greater.

27. An endoscopic surgical grasper device comprising:
   a member having a handle member and first and second grasping arms;
   first and second grasping elements attached to the first and second grasping arms respectively, and positioned on the arms in an opposed facing relationship to enable grasping of a targeted surface between the elements; and
   a gripping material on the surface of one or both of the grasping elements, the material providing enhanced holding power to the targeted surface relative to the holding power provided by the elements in the absence of the gripping material.

28. A method for manipulating tissue in an endoscopic surgical procedure, comprising:
   (a) providing an endoscopic surgical grasper device that comprises (i) a housing member having a handle member at a proximal end and first and second grasping arms at a distal end; (ii) first and second grasping elements attached to the first and second grasping arms respectively, and positioned on the arms in an opposed facing relationship to enable grasping of a targeted surface between the elements; and (iii) gripping element on one or both of the grasping elements, the material providing enhanced holding power to the targeted surface relative to the holding power provided by the elements in the absence of the gripping material;
   (b) in an endoscopic surgical procedure, introducing the grasper device into a patient and manipulating tissue of the patient with the grasper device.

29. The method of claim 28 wherein the grasper device is introduced into a patient through a trocar.

30. The method of claim 28 wherein the gripping material is substantially smooth.

31. The method of claim 28 wherein the gripping material has a coefficient of friction of about 0.6 or greater.

32. The method of claim 28 wherein the gripping material is a porous polymeric material or a non-woven material having a relative area surface roughness of between about 1.08 and 4.5.

* * * * *